United States Patent

Kosugi et al.

Patent Number: 6,001,626
Date of Patent: Dec. 14, 1999

[54] THERMOPHILIC PHOSPHOLIPASES AND METHOD FOR PRODUCTION THEREOF

[75] Inventors: Yoshitsugu Kosugi; Katsuhiko Higuchi; Kazuhiko Ishikawa; Ikuo Matsui, all of Ibaraki, Japan; Joh Yong-Goe, Pusan, Rep. of Korea

[73] Assignee: Director-General of Agency of Industrial Science and Technology, Japan

[21] Appl. No.: 08/982,312

[22] Filed: Dec. 1, 1997

[30] Foreign Application Priority Data

Dec. 2, 1996 [JP] Japan .................................. 8-321480

[51] Int. Cl.⁶ ...................................................... C12N 9/18
[52] U.S. Cl. .............................................................. 435/197
[58] Field of Search ................................................ 435/197

[56] References Cited

PUBLICATIONS

Adams et al. Chem. Eng. News, vol. 73(50), pp. 32–42, "Enzymes from Microorganisms in Extreme Environments", Dec. 1995.

Sako et al., Int. J. Syst. Bacteriol., vol. 46(4), "*Aeropyrum pernix* gen. nov., sp. nov., A Novel Aerobic Hyperthermophilic Archaeon Growing at Temperatures Up to 100 Degrees C.", pp. 1070–1077, 1996.

Hartley et al., Biochem. Soc. Symp., vol. 48, "Industrial Prospects for Thermophiles and Thermophilic Enzymes", pp. 133–146, 1983.

Wiegel et al., Crit. Rev. Biotechnol., vol. 3(1), "The Importance of Thermophilic Bacteria in Biotechnology", pp. 39–108, 1986.

Gonzalez et al. Extremophiles, vol. 2(2), "*Pyrococcus horikoshii* sp. nov., A Hyperthermophilic Archaeon isolated from a Hydrothermal Vent at the Okinawa Trough", pp. 123–130, 1998.

Brennan, M., Chem. Eng. News, vol. 74(42), "Enzyme Discovery Heats Up", pp. 31–33, Oct. 1996.

Aura et al,. Transesterification of Soy Lecithin by Lipase and Phospholipase, J. Am. Oil Chem. Soc. 72 (1995), 1375–1379.

Dahlke et al., First Experiences with Enzymatic Oil Refining, Inform, 6 (1995), 1284–1291.

Kleuser et al., Measurement of Phospholipase $A_2$ and 1–alkylglycerophosphocholine acetyltransferase Activities in Stimulated Alveolar Macrophages by HPLC Analysis of NBD–Labeled Ether Lipids, Chem. Phys. Lipid 79 (1996), 29–37.

Ohara et al., Protein, Nucleic Acid and Enzyme, 37 (1992), 898–905.

Shen & Cho, Highly Efficient Immobilization of Phospholipase $A_2$ and its Biomedical Applications, J. Lipid Res. 36 (1995), 1147–1151.

Washburn & Dennis, Novel General Approach for the Assay and Inhibition of Hydrolytic Enzymes Utilizing Suicide–Inhibitory Bifunctionally Linked Substrates (SIBLINKS): Exemplified by a Phospholipase $A_2$ Assay, J. Am. Chem. Soc. 112 (1990) 2040–2041.

*Primary Examiner*—Jon P. Weber
*Attorney, Agent, or Firm*—Finnegan, Henderson, Farabow, Garrett & Dunner

[57] ABSTRACT

Disclosed are a thermophilic phospholipase having an optimum temperature range of 95 to 105° C. which is useful in high-temperature degumming processes in oil refining process and high-temperature processing of phospholipids; and a method for producing a thermophilic phospholipase comprising culturing a microorganism capable of producing the phospholipase in a culture medium and collecting the phospholipase from the resultant culture.

5 Claims, 1 Drawing Sheet

THERMOPHILIC PHOSPHOLIPASES AND METHOD FOR PRODUCTION THEREOF

BACKGROUND OF THE INVENTION

1. Field of the Invention

The invention relates to thermophilic phospholipases and a method for producing the phospholipases. More particularly, the invention relates to novel thermophilic phospholipases useful in degumming processes and widely applicable to the oil chemical industry and the pharmaceutical industry, as well as a method for producing the phospholipases.

2. Description of Prior Art

To date, phospholipase $A_2$ has been used as an agent for treating hypercholestelemia [J. Lipid Res. 36, 1147 (1995)], and phospholipase $A_1$ and phospholipase $A_2$ have been used for production of lysophospholipids useful as a surfactant [J. Am. Oil Chem. Soc. 72, 1375 (1995)].

Phospholipase $A_2$ has also been used in oil refining processes. When phospholipase $A_2$ is introduced into degumming processes in oil refining, it becomes possible to reduce the phosphorous content to a level of 8 ppm or below, and thus simple physical oil refining processes become applicable. As a result, the oil refining process using phospholipase $A_2$ is used in its degumming processes has successfully reduced the amount of water consumption to ⅛ based on that of conventional processes and the steam cost to 5.27 dollars/ton which was 9.19 dollars/ton in conventional processes (Inform, 6, 1284 (1995)).

As mentioned above, phospholipases have been widely used in various fields. However, since such phospholipases are originated from higher organisms, they are limited in yield and properties such as thermostability. In particular, in these processes, in which high temperature circumstances are desired such as degumming processes in oil refining, thermophilic phospholipases which do not lose their enzymatic activity even at high temperatures have been strongly demanded.

However, such thermophilic phospholipases have not been reported yet.

SUMMARY OF THE INVENTION

In these situations, the present inventors have made intensive and extensive studies for solving the above-mentioned problems, paying attention to hyperthermophilic bacteria capable of growing at 90–100° C. or higher and the phospholipase production properties thereof. As a result, the present inventors have found thermophilic phospholipases which do not loss their enzymatic activity at high temperatures.

Accordingly, the present invention relates to a thermophilic phospholipase having an optimum temperature range of 95° C. to 105° C. Specific examples of the thermophilic phospholipase include thermophilic phospholipase $A_1$ and thermophilic phospholipase $A_2$.

Further, the present invention relates to a method for producing a thermophilic phospholipase comprising culturing a microorganism capable of producing the phospholipase in a culture medium and collecting the phospholipase from the culture. Examples of such microorganism include hyperthermophilic archaea belonging to the genus Pyrococcus or Aeropyrum. In the method, the culturing of the microorganism is conducted at as high as 75 to 105° C.

It is also possible to produce the above-mentioned thermophilic phospholipase in a large scale by purifying the phospholipase protein, determining a part of the amino acid sequence thereof, obtaining a phospholipase gene by PCR using the genomic DNA of a microorganism belonging to the genus Pyrococcus or Aeropyrum as a template and a DNA sequence corresponding to the above partial amino acid sequence as a probe, determining the DNA sequence of the gene, incorporating the gene into a plasmid to obtain an expression plasmid, transforming a host microorganism such as *Escherichia coli, Bcillus subtilis,* yeast and filamentous fungi with the expression plasmid to obtain a transformed microorganism, and culturing the transformed microorganism.

DETAILED DESCRIPTION OF THE INVENTION

Figure 1:
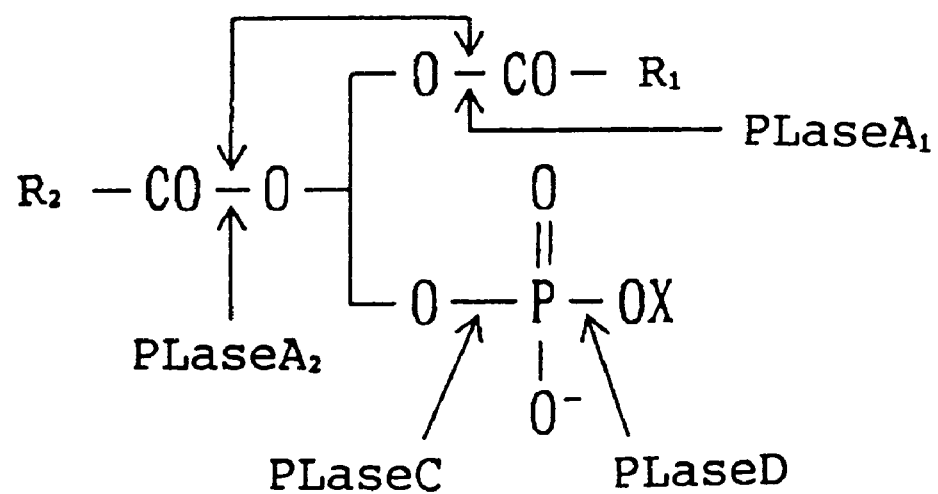
FIG. 1 illustrates the cleavage sites of phospholipids by various phospholipases.

The present invention will be described more specifically.

As used herein, the term "hyperthermophilic archaea" means thermophilic archaea capable of growing at especially high temperatures which have a growth optimum temperature range of 90 to 105° C. and which exhibit little growth at 70° C. or below.

The hyperthermopilic archaea used in the present invention are sulfer-metabolizable thermophilic archaea. Examples of such archaea include those belonging to the genera Pyrococcus, Pyrodictium, Thermoproteus and Aeropyrum. Among them, archaea belonging to the genera Pyrococcus and Aeropyrum are most preferable. Microorganisms belonging to the genus Pyrococcus are strictly anaerobic cocci which require powdered sulfur for their growth and grow as generating hydrogen sulfide therefrom. Specific examples of such microorganisms include *Pyrococcus horikoshii* which has a growth temperature range of 75 to 104° C., a genome size of 2000 kbp and a GC-content of 41% and *Pyrococcus furiosus which has a growth temperature range of 75 to 105° C.,* a genome size of 1800 kbp and a GC-content of 38%. The microorganisms *Pyrococcus horikoshii* (FERM BP-6771), *Pyrococcus furiosus* (FERM BP-6772), and *Aeropyrum pernix* (FERM BP-6773) have been deposited in the National Institute of Bioscience and Human-Technology Agency of Industrial Science and Technology, having its principal place of business at 1–3, Higashi 1-chome, Tsukuba-shi, Ibaraki-ken, Japan. *Aeropyrum pernix* may also be used in the present invention, which is a strictly aerobic hyperthermophilic archaeon having a growth temperature range of 70 to 100° C., a growth pH range of 5 to 9, a growth salt concentration range of 1.8 to 7% and a GC content of 67% (Int. J. Syst. Bacteriol., 46, 1070–1077(1996)).

Cultivation of a hyperthermophilic archaeon belonging to the genus Pyrococcus used in the present invention and collection of the phospholipase from the culture are conducted in the following manner. An aqueous solution comprising NaCl, $Na_2SO_4$, KCl, $NaHCO_3$, KBr, $H_3BO_3$, $MgCl_2@6H_2O$, $CaCl_2$, $SrCl_2$, resazurin solution, yeast extract and Bacto-Peptone is prepared and then sterilized in an autoclave under pressure. To this solution is added sulfur powder which has been separately sterilized with hot air at 100° C. to prepare a medium. The medium is saturated with argon or carbon dioxide and confirmed to have reached to a strictly anaerobic state by adding $Na_2S$ solution to the medium and observing that its pink color disappears. Thereafter, a predetermined amount of archaeal cells are inoculated into the medium and anaerobically cultured in an anaerobic jar. The cultivation is preferably conducted at a temperature ranging from 75 to 105° C. which is the growth temperature for the hyperthermophilic archaeon of the invention, more preferably at a temperature ranging from 90 to 95° C. to enhance the growth of the archaeon. The cultivation time is one to two days at 95° C., which is relatively short. With respect to *Aeropyrum pernix,* cultivation of this archaeon is conducted aerobically in artificial seawater as a basal medium at 90° C. with shaking [Int. J. Syst. Bacteriol., 46, 1070–1077 (1996)].

The hyperthermophilic archaea used in the present invention are capable of growing at a temperature range of 75 to 105° C., and the thermophilic phospholipase produced as mentioned in Example 1 below is suitable for use at high temperatures such as in degumming processes in refining of oils and fats.

The thus-produced thermophilic enzyme has enzymatic activity(ies) of phospholipase $A_1$ and/or phospholipase $A_2$ and, therefore, the product from the enzyme reaction exhibits a surface activating property but exhibits no decomposing activity on oils and fats. From these reasons, the thermophilic phospholipase of the present invention is extremely useful for the above-mentioned processes.

"Phospholipase" is a generic name for enzymes catalyzing the hydrolysis of phospholipids and classified into four subgroups of phospholipases $A_1$, $A_2$, C and D depending on the cleavage site by the hydrolysis of the phospholipids.

Phospholipids are a main lipid composing various membrane systems in organisms-constituting cells such as plasmalemma, nuclear membrane and cell membrane. They are roughly classified into glycerophospholipids and sphingophospholipids. Examples of typical glycerophospholipids include phosphatidylcholine, phosphatidylserine, phosphatidylinositol, phosphatidylethanolamine and phosphatidylglycerol, which are preferable substrates for phospholipases.

Phospholipase $A_1$ is a membrane-bound enzyme which is widely distributed in various organisms. Phospholipase $A_2$ is known to be distributed in toxins of snakes or bees or mammalian pancreatic juice (Ohara et al., Protein, Nucleic Acid and Enzyme, 37, 898 (1992)). The cleavage sites by various phospholipases in phospholipids are shown in FIG. 1. In FIG. 1, $R_1$ and $R_2$ individually represent a hydrocarbon chain of a fatty acid, and generally $R_1$ represents a saturated hydrocarbon chain and $R_2$ represents an unsaturated hydrocarbon chain; X represents a residue such as choline, ethanolamine, serine and inositol; arrows marked with $A_1$, $A_2$, C and D indicate cleavage sites by phospholipases $A_1$, $A_2$, C and D, respectively.

As shown in FIG. 1, phospholipase $A_1$ can decompose, for example, phosphatidylserine, phosphatidylethanolamine, phosphatidylinositol or phosphatidylcholine. Accordingly, when any of L-α-phosphatidylcholine-β-oleoyl-γ-palmitoyl, L-α-phosphatidylcholine-β-oleoyl-γ-stearoyl, L-α-phosphatidylcholine-β-palmitoyl-γ-oleoyl and L-α-phosphatidylcholine-β-linoleoyl-γ-stearoyl is used as a substrate, phospholipase $A_1$ decomposes these substances to release palmitic acid, stearic acid, oleic acid and stearic acid, respectively, which are compounds derived from the γ-positions of the above substances.

Phospholipase $A_2$ acts on, for example, phosphatidylserine, phosphatidylethanolamine, phosphatidylinositol and phosphatidylcholine. For example, when phospholipase $A_2$ is used to decompose phosphatidylcholine, lysophosphatidylcholine and a fatty acid are released. Accordingly, when any of L-α-phosphatidylcholine-β-oleoyl-γ-palmitoyl, L-α-phosphatidylcholine-β-oleoyl-γ-stearoyl, L-α-phosphatidylcholine-β-palmitoyl-γ-oleoyl and L-α-phosphatidylcholine-β-linoleoyl-γ-stearoyl is used as a substrate, phospholipase $A_2$ decomposes these substances to release oleic acid, oleic acid, palmitic acid and linolenic acid, respectively.

The substrates for the thermophilic phospholipases of the present invention are glycerophospholipids such as phosphatidylserine, phosphatidylethanolamine, phosphatidylinositol, and phosphatidylcholine. With respect to substrate specificity, phosphatidylserine is the most appropriate, followed by phosphatidylethanolamine, phosphatidylinositol and phoisphatidylcholine in turn.

The thermophilic phospholipases produced by the hyperthermophilic archaea of the present invention are different from the conventional secretory phospholipase $A_1$ and phospholipase $A_2$ from the pancreas, snake toxins, etc. which have been studied and put into practical use. This difference has been confirmed from the facts that the above-mentioned enzymatic activities are observed not in the culture supernatant but in the cell fraction of the above-mentioned hyperthermophilic archaea and that the enzymes of the invention are not inhibited by dithiothreitol (DTT) which is an inhibitor specific to secretory phospholipases.

The thermophilic phospholipases produced by the hyperthermophilic archaea of the present invention are high temperature-reactive enzymes exhibiting their enzymatic activity at 75° C. or above and their optimum temperature range of 95 to 105° C. Such a high optimum temperature range is the most characteristic feature of the thermophilic phospholipases of the present invention. Since the thermophilic phospholipases do not decompose triacylglycerols such as triolein, tristearin and trimyristin even at 95° C., they are specific to phospholipids.

Generally, the quantitative determination of an enzyme is conducted by reacting the enzyme with a substrate at a specific temperature and determining the amount of the reaction product in the reaction solution.

For the quantitative determination of the thermophilic phospholipase of the present invention exhibiting enzymatic activity at higher temperatures, a thermostable substrate labeled with a fluorescent substance such as N-(7-nitrosobenzo-2-oxa-1,3-thizol-4-yl) (hereinafter, referred to as "NBD") is used. The use of such NBD-labeled fluorescent substrate enables to detect by a fluorescence detection method a NBD acid decomposed and released from the substrate by a high temperature-reactive thermophilic phospholipase having an optimum temperature around 95° C. with a great precision. In case of the determination using a glycerophospholipid as a substrate, the determination should be conducted under conditions where the substrate is never decomposed non-enzymatically. In general, when a conventional substrate is used, the determination of the fatty acid decomposed and released from the substrate is conducted at a reaction temperature ranging from 70 to 75° C. However, since the thermophilic phospholipases of the present invention have their optimum temperature around 95° C., when they are reacted with a glycerophospholipid at temperatures near the optimum temperature, non-enzymatic decomposition of the glycerophospholipid will occur. When the above-mentioned NBD is used as a labeling compound, the thermophilic phospholipase of the present invention can be quantitatively determined without occurrence of any non-enzymatic decomposition.

The reaction of a substrate with the thermophilic phospholipase of the present invention is conducted at a high temperature ranging from 75 to 105° C. for an appropriate period of time as described above prior to the termination of the reaction. The reaction time may vary depending on the production rate of the reaction product. However, it is preferable to conduct the determination of the enzymatic activity in a time region where the amount of the reaction product obtained is proportional to the amount of the enzyme used. In addition, in the reaction of the substrate with the thermophilic phospholipase, addition of a compound capable of solubilizing the thermophilic phospholipase into the reaction system can enhance the enzymatic activity of the enzyme. Examples of such compound include sodium cholate, sodium deoxycholate, SDS (sodium dodecyl sulfate) and octyl glycoside. Among them, sodium cholate is preferred because of its less influence on enzyme proteins.

The reaction is terminated by adding a mixture of appropriate solvents to the reaction solution after it has been ice-cooled. A preferred solvent mixture is, for example, a chloroform:methanol: acetic acid system (10:20:0.6).

After terminating the reaction, almost equal volumes of water and an organic solvent are added to the reaction solution and mixed. The reaction product extracted to the organic solvent phase is identified and quantitatively determined. For the separation, identification and quantitative determination, it is preferable to use high performance liquid chromatography (HPLC) using a normal phase column in terms of good sensitivity. As the eluent, a chloroform-methanol system may be used. The use of a chloroform-water-methanol-acetic acid system (500:350:45:45) as the eluent provides complete separation between the reaction product and the substrate.

With respect to the method for analysis of the fatty acid, any method may be employed as long as it can detect the labeling substance. However, when a fluorescent substance is used for the labeling of the substrate, a fluorescence analysis should be conducted, in which the wavelength of excitation light and the wavelength of detection light are properly selected depending on the structure of the labeling substance used.

In this manner, the fatty acid released by the thermophilic phospholipase produced by the hyperthermophilic archaea of the present invention can be detected precisely and simply and with high sensitivity.

EXAMPLES

For illustrating the invention in more detail, examples using *Pyrococcus horikoshii* are described below.

Example 1

Cultivation of the Bacterium and Detection of Fractions with Thremophilic Phospholipse Activity (1) Cultivation of Bacteria To one litter of distilled water were added and dissolved 13.5 g of NaCl, 4 g of $Na_2SO_4$, 0.7 g of KCL, 0.2 g of $NaHCO_3$, 0.1 g of KBr, 30 mg of $H_3BO_3$, 10 g of $MgCl_2$. $6H_2O$, 1.5 g of $CaCl_2$, 25 mg of $SrCl_2$, 1.0 ml of resuzurin solution (0.2 g/L), 1.0 g of yeast extract and 5 g of Bacto-Peptone. The pH of the solution was adjusted to 6.8 and then the solution was sterilized under pressure. Subsequently, 0.2 g of sulfur powder which had been sterilized with hot air at 100° C. was added to the resultant solution to obtain a culture medium. After the medium was saturated with argon to make it anaerobic, *Pyrococcus horikoshii* JCM 9974 was inoculated to the medium. The anaerobicity of the medium was confirmed by adding $Na_2S$ solution to the medium and observing that no pink color is formed due to the resuzurin solution. The culturing was conducted at 95° C. for 1–4 days and then the resultant culture solution was centrifuged.

(2) Determination of Fractions with Thermophilic Phospholipase Activity

To a solution containing 2 mg of phosphatidylcholine and 40 μl of 100 mM sodium cholate, 0.5 mL of the cell suspension from (1) above was added and the resultant mixture was cultured at 75° C. overnight. Five μL of the resultant reaction solution was subjected to TLC analysis with a developing solvent (chloroform:methanol:water= 65:25:4) to confirm the production of lysophosphatidylcholine. On the other hand, an aliquot of the reaction solution was also subjected to TLC analysis with a developing solvent (chloroform:acetone:methanol=94:5.5:0.5) to confirm the production of a fatty acid. However, when the above-obtained culture solution was centrifuged using a 30 cm-roter at 6,000 rpm, the culture supernatant fractions showed no production of the above-mentioned products.

Accordingly, the thermophilic phospholipase activity was detected in the cell fractions, but not in the culture supernatant containing secreted substances from the hyperthermophilic archaeon.

When 100 μL (final concentration: 3 mM) of 20 mM calcium chloride was added to the reaction mixture comprising the cell fraction, the amount of the reaction product increased.

(3) Behavior of Secretory Phospholipases Against an Inhibitor

Inhibition by dithiothreitol (DTT) which is an inhibitor specific to conventional secretory phospholipases was examined.

To 500 μL of the cell fraction containing the thermophilic phospholipase of the present invention was added 16–160 μL of 100 μM DTT along with a reaction solution containing 4 mg of phosphatidylcholine or phosphatidylethanolamine as a substrate. The resultant reaction solution, which contained DTT at a concentration of 0 mm, 1.8 mM, 3.0 mM, 9.8 mM or 20 mM. Then, the enzyme reaction product therein was confirmed by TLC, and it was checked whether the amount of the fatty acid produced has been decreased with increased concentration of DTT. As a result, the amount of the fatty acid released was the maximum when the concentration of DTT was 3.0 mM, and the amount decreased little even when the concentration of DTT was 20 mM. These facts evidently show that the thermophilic phospholipase is not inhibited by DTT.

From the above, it has become clear that the activity of the thermophilic phospholipase of the present invention is detected not in the culture supernatant but in the cell fraction, and that this thermophilic phospholipase is different from other conventional secretory phospholipases in behavior against the inhibitor (DTT).

Example 2

Analysis of Reaction Products

As the substrates, L-α-phosphatidylcholine-β-oleoyl-γ-palmitoyl, L-α-phosphatidylcholine-β-oleoyl-γ-stearoyl, L-α-phosphatidylcholine-β-palmitoyl-γ-oleoyl and L-α-phosphatidylcholine-β-linoleoyl-γ-stearoyl were used.

To 0.5 mL of a cultured cell fraction of *Pyrococcus horikoshii* JCM 9974 were added 2 mg of each of these substrates, 40 μl of 100 mM sodium cholate and 100 μL of 20 mM calcium chloride. The resultant reaction solution was reacted at 75° C. overnight. From the reaction solution, a fraction containing the fatty acid produced was extracted with isooctane and then subjected to gas chromatography. As a result, a decomposition product including 47–48% of oleic acid, oleic acid, palmitic acid or linolenic acid resulted from the decomposition by phospholipase $A_2$ and 47–48% of palmitic acid, stearic acid, oleic acid or stearic acid resulted from the decomposition by phospholipase $A_1$ was obtained from each of the substrates.

As described above, it has become apparent that *Pyrococcus horikoshii* used in the present invention has an ability to produce phospholipase $A_1$ and phospholipase $A_2$.

Example 3

(1) Selection of the Substrate

As the substrates to be tested, L-α-phosphatidylcholine-β-(NBD-aminohexanoyl)-γ-palmitoyl and 1-decanoyl-2-(p-nitrophenylglutaryl)phosphatidylcholine were used.

When NBD-acid [N-(7-nitrobenz-2-oxa-1,3-diazol-4-yl) aminohexanoic acid] was produced from the substrate L-α-phosphatidylcholine-β-(NBD-aminohexanoyl)-γ-palmitoyl, its suitability was examined according to the method by B. Kleuser et al. (Chem. Phys. Lipid. 79, 29 (1996)). When p-nitrophenol was produced from the substrate 1-decanoyl-2-(p-nitrophenylglutaryl)phosphatidylcholine, its suitability was examined according to the method by W. N. Washburn et al. (J. Am. Chem. Soc. 112, 2040 (1990)). In either case, sodium cholate was added to the reaction solution to solubilize the enzyme into the solution.

The method by B. Kleuser et al. is a method in which the above mentioned fluorescent substrate and the product therefrom are detected by their emission of fluorescence. Since it was confirmed by the fluorescent determination that non-enzymatic thermolysis does not occur at 95–105° C. with the above substrate, this substrate is judged to be effective for determination of the thermophilic phospholipase activity.

On the other hand, the result given by the method of W. N. Washburn et al. was that the substrate was readily decomposed non-enzymatically by merely adding 100 mM sodium cholate (100 µL) to the reaction solution (640 µL) at a high temperature (about 70–95° C.).

From these results, 1-decanoyl-2-(p-nitrophenylglutaryl) phosphatidylcholine was judged to be unsuitable as the substrate for determination of the thermophilic phospholipase $A_2$.

(2) Determination of the Reaction Optimum Temperature

Twenty µg of L-α-phosphatidylcholine-β-(NBD-aminohexanoyl)-γ-palmitoyl (as a substrate), 40 µL of 100 mM sodium cholate and 100 µL of 20 mM calcium chloride were mixed and 400 µL of a cell dilution (1 mg/mL) was added thereto. The resultant mixed solution was reacted at each of the temperatures indicated in Table 1 below (i.e., 75° C., 85° C., 95° C. and 105° C.) for 30 min. and then cooled on ice. To the ice-cooled reaction solution were added an ice-cooled mixture of chloroform:methanol:acetic acid (10:20:0.6) and additionally 1.25 mL of 0.9% aqueous NaCl solution (its pH was adjusted to 2.0 with dilute hydrochloric acid) and 1.25 mL of dichloromethane, followed by mixing.

The resultant mixture was centrifuged at 500 g for 5 min. and then the upper phase (i.e., aqueous phase) was discarded and the lower phase (i.e., organic phase) was dried under nitrogen stream. The residue thus dried was dissolved in 200 µL of ethanol, and 5 µL of the solution was subjected to high performance liquid chromatography (HPLC). The conditions for the HPLC were as follows:

Column: Partisil-(4.6 mm×250 mm, GL Science);
Eluent:chloroform:methanol:water:acetic acid= 500:250:45:45;
Flow rate: 1.5 mL/min.;
Detector: Shimadzu fluorescence detector;
Wavelength of excitation light: 450 nm; and
Wavelength of detection light: 510 nm.

When the fluorescence detection was conducted using excitation light of 450 nm and detection light of 510 nm, fluorescence peaks for the product released from the substrate and the remaining unreacted substrate were observed, respectively.

From these peak values, the enzymatic activity at temperature as indicated in Table 1 below was calculated as relative activity (%) by the peak area method to compare with each other. The results are shown in Table 1.

TABLE 1

| Tem. (° C.) | Relative Activity (%) |
|---|---|
| 75 | 29 |
| 85 | 48 |
| 95 | 100 |
| 105 | 67 |

As shown in Table 1, the reaction optimum temperature of the thermophilic phospholipase produced by the hyperthermophilic archaeon of the present invention fell within the range of 95 to 105° C., and the maximum relative activity was obtained at 95° C.

Subsequently, substantially the same procedure as mentioned above was repeated for determination of the optimum pH for the phospholipase using the enzyme in 0.5 mL of phosphate buffer (pH 6.0, 6.6, 7.2 and 8.2) at 93° C. for 40 min. The result was that the optimum pH fell within the range of 6.6–7.2, and the maximum relative activity was obtained at pH 7.2.

Example 4

Evaluation of Reactivity on Substrates

The reactivity of the thermophilic phospholipase on substrates was evaluated using phosphatidylserine, phosphatidylethanolamine and phosphatidylinositol as the substrates.

As a result, the degree of the thermophilic enzyme produced by the hyperthermophilic archaeon of the present invention on the substrates was as follows: phosphatidylserine>phosphatidylethanolamine>phosphatidylinositol>phosphatidylchorine. This reactivity was confirmed by analyzing each reaction product by thin-layer chromatography (TLC) with a developing solvent (chloroform:methanol:water=65:25:4).

When egg yolk lecithin was decomposed with the above-mentioned enzyme, palmitic acid, oleic acid, linoleic acid and arachidonic acid were released as major fatty acids. These free fatty acids were determined by TLC with a developing solvent (chloroform:acetone:methanol= 94:5.5:0.5). The above-mentioned substrate-specificity was determined at 75° C. When triolein, tristearin and trimyristin were also reacted with the above-mentioned enzyme in the same manner as mentioned above, no free fatty acid was detected. Triacylglycerol was not decomposed with the above-mentioned enzyme even at 95° C.

Effect of the Invention

According to the present invention, thermophilic phospholipases having an optimum reaction temperature range of 95–105° C. are provided. The enzymes of the present invention are useful for degumming in oil-refining processes conducted at high temperatures and for processing phospholipids at high temperatures.

What is claimed is:

1. An isolated thermophilic phospholipase having an optimum temperature range of 95 to 105° C. wherein the thermophilic phospholipase is derived from a hyperthermophilic archaea.

2. The thermophilic phospholipase according to claim 1, which is thermophilic phospholipase $A_1$ and/or thermophilic phospholipase $A_2$.

3. A method for producing a thermophilic phospholipase having an optimum temperature range of 95 to 105° C. and being derived from a hyperthermophilic archaea, comprising culturing said hyperthermophilic archaea capable of producing said phospholipase in a culture medium and collecting the phospholipase from the resultant culture.

4. The method according to claim 3, wherein said hyperthermophilic archaea is one belonging to the genus Pyrococcus or Aeropyrum.

5. The method according to claim 3, wherein said thermophilic phospholipase is thermophilic phospholipase $A_1$ or thermophilic phospholipase $A_2$.

* * * * *

UNITED STATES PATENT AND TRADEMARK OFFICE
CERTIFICATE OF CORRECTION

PATENT NO.     : 6,001,626
DATED          : December 14, 1999
INVENTOR(S)    : Kosugi et al.

It is certified that error appears in the above-identified patent and that said Letters Patent is hereby corrected as shown below:

<u>Title page,</u>
Item [57], ABSTRACT,
Line 1, "are" should read -- is --.

Signed and Sealed this

Third Day of December, 2002

JAMES E. ROGAN
*Director of the United States Patent and Trademark Office*